US006410302B1

(12) United States Patent
Träff et al.

(10) Patent No.: US 6,410,302 B1
(45) Date of Patent: *Jun. 25, 2002

(54) GENETICALLY ENGINEERED YEAST AND MUTANTS THEREOF FOR THE EFFICIENT FERMENTATION OF LIGNOCELLULOSE HYDROLYSATES

(75) Inventors: K. L. Träff, Lund (SE); R. R. Cordero Otero; W. H. Van Zyl, both of Stellenbosch (ZA); B. Hahn-Hägerdal, Lund (SE)

(73) Assignee: Forskarpatent I Syd AB, Lund (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/294,894

(22) Filed: Apr. 20, 1999

Related U.S. Application Data
(60) Provisional application No. 60/082,334, filed on Apr. 20, 1998.

(51) Int. Cl.$^7$ .............................. C12N 1/14; C12N 15/00

(52) U.S. Cl. .................................. 435/254.2; 435/320.1

(58) Field of Search ........................... 435/254.2, 320.1

(56) References Cited

FOREIGN PATENT DOCUMENTS

| EP | 0450430 A2 | * | 3/1991 |
| WO | 91/06660 | * | 5/1991 |
| WO | 91/15588 | | 10/1991 |
| WO | 95/13362 | | 5/1995 |
| WO | 97/42307 | | 11/1997 |

OTHER PUBLICATIONS

Johnston et al., Science, 265(5181), 2077–2082, Sep. 1994.*
Strasser et al., DE 4009676A, See the Sequence Alignment, Oct. 1991.*
Cherry, J.M., et al., "Genetic and Physical Maps of Saccharomyces Cerevisiae", *Nature* 387(6632S):67–73, May 29, 1997.
Goffeau, A., et al., "Life with 6000 Genes", *Science* 274:546–567, Oct. 25, 1996.
Lee, H., "The Structure and Function of Yeast Xylose (Aldose) Reductases", *Yeast* 14:977–984, 1998.
Magdolen, V., et al., "Transcriptional Control by Galactose of a Yeast Gene Encoding a Protein Homologous to Mammalian Aldo/Keto Reductases", *Gene* 90(1):105–114, May 31, 1990.
Nakajima, N., et al, "Differences in Protein Structure and Similarities in Catalytic Function of Two L–Stereoselective Carbonyl Reductases from Bakers' Yeast", *Biosci. Biotech. Biochem.* 58(11):2080–2081, 1994.

Norbeck, J., et al., "Metabolic and Regulatory Changes Associated with Growth of Saccharomyces Cerevisiae in 1.4 M NaCl", *Journal of Biological Chemistry* 272(9):5544–5554, Feb. 29, 1997.
Oechsner, U., et al., "A Nuclear Yeast Gene (GCY) Encodes a Polypeptide with High Homology to a Vertebrate Eye Lens Protein", *FEBS Letters* 238(1):123–128, Sep. 26, 1988.
Robinson, B., et al., "Aldose and Aldehyde Reductases From Human Kidney Cortex and Medulla", *Biochimica et Biophysica Acta* 1203(2):260–266, Dec. 1993.
Vander Jagt, D.L., et al., "Aldehyde and Aldose Reductases from Human Placenta. Heterogeneous Expression of Multiple Enzyme Forms", *Journal of Biological Chemistry* 265(19):10912–10918, Jul. 5, 1990.
Vander Jagt, D.L., et al., "Substrate Specificity of Human Aldose Reductase: Identification of 4–Hydroxynonenal as an Endogenous Substrate", *Biochimica et Biophysica Acta.* 1249(2):117–126, Jun. 12, 1995.
Verduyn, C., et al., "Multiple Forms of Xylose Reductase in Pachysolen Tannophilus", *FEMS Microbiology Letters* 30:313–317, 1985.
K. Dekker et al., "Xylose (Glucose) Isomerase Gene from the Thermophile *Thermus thermophilus*: Cloning, Sequencing, and Comparison with Other Thermostable *Thermus thermophilus*: Cloning, Sequencing, and Comparison with Other Thermostable Xylose Isomerases," *J. Bacteriol.*, vol. 173, No. 10, May 1991, pp. 3078–3083.
M. Walfridsson et al., "Ethanolic Fermentation of Xylose with *Saccharomyces cerevisiae* Harboring the *Thermus thermophilus xylA* Gene, Which Expresses an Active Xylose (Glucose) Isomerase," *Appl. Environ. Microbiol.*, vol. 62, No. 12, Dec. 1996, pp. 4648–4651.
M. Moniruzzaman et al., "Fermentation of Corn Fibre Sugars by an Engineered Xylose Utilizing *Saccharomyces* Yeast Strain," *World J. Microbiol. Biotechnol.*, vol. 13, No. 3, May 1997, pp. 341–346.

(List continued on next page.)

*Primary Examiner*—Rebecca E. Prouty
*Assistant Examiner*—Maryam Monshipouri
(74) *Attorney, Agent, or Firm*—Finnegan, Henderson, Farabow, Garrett & Dunner, LLP

(57) ABSTRACT

The present invention provides genetically engineered expression vectors, and recombinant cells comprising those vectors, or portions of those vectors. The vectors comprise a mutant form of a gene encoding an aldose reductase (AR) enzyme in which only a portion of the gene is present on the vector. The mutated aldose reductase sequence serves as a site for homologous crossing over of vector-encoded sequences and a host cell genome. Recombinant cells made using the vector of the invention lack an aldose reductase gene and are capable of fermenting lignocellulose hydrolysates to ethanol in high quantities. The invention also provides recombinant vectors and cells with multiple copies of genes encoding enzymes involved in the conversion of lignocellulose or lignocellulose hydrolysates to ethanol. Accordingly, the invention provides methods of making recombinant cells and methods of efficiently producing ethanol from lignocellulose-containing compositions.

8 Claims, 4 Drawing Sheets

OTHER PUBLICATIONS

P. Kotter et al., "Xylose Fermentation by *Saccharomyces cerevisiae*," *Appl. Microbiol. Biotechnol.*, vol. 38, No. 6, Mar. 1993, pp. 776–783.

M. Walfridsson et al., "Xylose–Metabolizing *Saccharomyces cerevisiae* Strains Overexpressing the TKL1 and TAL1 Genes Encoding the Pentose Phosphate Pathway Enzymes Transketolase and Transaldolase," *Appl. Env. Micorbioi.* vol. 61, No. 12, Dec. 1995, pp. 4184–4190.

M. Walfridsson et al., "Expression of Different Levels of Enzymes from the *Pichia stipitis* XYL1 and XYL2 Genes in *Saccharomyces cerevisiae* and Its Effect on Product Formation During Xylose Utilisation," *Appl. Microbiol. Biotechnol.*, vol. 48, No. 2, Aug. 1997, pp. 218–224.

Xue Xing Deng et al., "Xylulokinase Activity in Various Yeasts Including *Saccharomyces cerevisiae* Containing the Cloned Xylulokinase Gene," *Appl. Biochem. Biotech.*, vol. 24/25, 1990, pp. 193–199.

S. Toon et al., "Enhanced Cofermentation of Glucose and Xylose by Recombinant *Saccharomyces* Yeast Strains in Batch and Continuous Operating Modes," *Appl. Biochem. Biotech.*, vol. 63–65, 1997, pp. 243–255.

A. Kuhn et al., "Purification and Partial Characterization of an Aldo–Keto Reductase from *Saccharomyces cerevisiae*," *Appl. Environ. Microbiol.*, vol. 61, No. 4, Apr. 1995, pp. 1580–1585.

* cited by examiner

SEQUENCE OF *S. CEREVISIAE* ALDOSE REDUCTASE GENE

Length: 1920

```
  1 CCG TGT TCA TCA AGA AAT GGG CGC ATT ACT ACA AGA AGT TTT      42

EcoRI
      GATCGAATTC
                TT TGT AAC TGT AAT TTC ACT CAT GC   << 1st left primer (SEQ ID NO:25)
 43 GAT ATT TTT TGT AAC TGT AAT TTC ACT CAT GCA CAA GAA AAA      84

85 AAA AAC TGG ATT AAA AGG GAG CCC AAG GAA AAC TCC TCA GCA     126

127 TAT ATT TAG AAG TCT CCT CAG CAT ATA GTT GTT TGT TTT CTT     168

169 TAC ACA TTC ACT GTT TAA TAA AAC TTT TAT AAT ATT TCA TTA     210

211 TCG GAA CTC TAG ATT CTA TAC TTG TTT CCC AAT TGT TGC TGG     252

253 TAG TAA ACG TAT ACG TCA TAA AAG GGA AAA GCC ACA TGC GGA     294

295 AGA ATT TTA TGG AAA AAA AAA AAA CCT CGA AGT TAC TAC TTC     336

337 TAG GGG GCC TAT CAA GTA AAT TAC TCC TGG TAC ACT GAA GTA     378

379 TAT AAG GGA TAT AGA AGC AAA TAG TTG TCA GTG CAA TCC TTC     420

421 AAG ACG ATT GGG AAA ATA CTG TAA TAT AAA TCG TAA AGG AAA     462
                 1st left primer   >>   TTT AGC ATT TCC TTT 463 ATT GGA AAT TTT TTA AAG ATG TCT TCA CTG GTT ACT CTT AAT     504
                            MET Ser Ser Leu Val Thr Leu Asn
    TAA CCT TT
         TTCGAACATG (SEQ ID NO: 26)
         HindIII 505 AAC GGT CTG AAA ATG CCC CTA GTC GGC TTA GGG TGC TGG AAA     546
    Asn Gly Leu Lys MET Pro Leu Val Gly Leu Gly Cys Trp Lys 547 ATT GAC AAA AAA GTC TGT GCG AAT CAA ATT TAT GAA GCT ATC     588
    Ile Asp Lys Lys Val Cys Ala Asn Gln Ile Tyr Glu Ala Ile 589 AAA TTA GGC TAC CGT TTA TTC GAT GGT GCT TGC GAC TAC GGC     630
    Lys Leu Gly Tyr Arg Leu Phe Asp Gly Ala Cys Asp Tyr Gly 631 AAC GAA AAG GAA GTT GGT GAA GGT ATC AGG AAA GCC ATC TCC     672
    Asn Glu Lys Glu Val Gly Glu Gly Ile Arg Lys Ala Ile Ser 673 GAA GGT CTT GTT TCT AGA AAG GAT ATA TTT GTT GTT TCA AAG     714
    Glu Gly Leu Val Ser Arg Lys Asp Ile Phe Val Val Ser Lys 715 TTA TGG AAC AAT TTT CAC CAT CCT GAT CAT GTA AAA TTA GCT     756
    Leu Trp Asn Asn Phe His His Pro Asp His Val Lys Leu Ala
```

FIG. 2A

```
 757 TTA AAG AAG ACC TTA AGC GAT ATG GGA CTT GAT TAT TTA GAC  798
     Leu Lys Lys Thr Leu Ser Asp MET Gly Leu Asp Tyr Leu Asp

799 CTG TAT TAT ATT CAC TTC CCA ATC GCC TTC AAA TAT GTT CCA  840
     Leu Tyr Tyr Ile His Phe Pro Ile Ala Phe Lys Tyr Val Pro

841 TTT GAA GAG AAA TAC CCT CCA GGA TTC TAT ACG GGC GCA GAT  882
     Phe Glu Glu Lys Tyr Pro Pro Gly Phe Tyr Thr Gly Ala Asp

883 GAC GAG AAG AAA GGT CAC ATC ACC GAA GCA CAT GTA CCA ATC  924
     Asp Glu Lys Lys Gly His Ile Thr Glu Ala His Val Pro Ile

925 ATA GAT ACG TAC CGG GCT CTG GAA GAA TGT GTT GAT GAA GGC  966
     Ile Asp Thr Tyr Arg Ala Leu Glu Glu Cys Val Asp Glu Gly

967 TTG ATT AAG TCT ATT GGT GTT TCC AAC TTT CAG GGA AGC TTG 1008
     Leu Ile Lys Ser Ile Gly Val Ser Asn Phe Gln Gly Ser Leu

1009 ATT CAA GAT TTA TTA CGT GGT TGT AGA ATC AAG CCC GTG GCT 1050
     Ile Gln Asp Leu Leu Arg Gly Cys Arg Ile Lys Pro Val Ala

1051 TTG CAA ATT GAA CAC CAT CCT TAT TTG ACT CAA GAA CAC CTA 1092
     Leu Gln Ile Glu His His Pro Tyr Leu Thr Gln Glu His Leu

1093 GTT GAG TTT TGT AAA TTA CAC GAT ATC CAA GTA GTT GCT TAC 1134
     Val Glu Phe Cys Lys Leu His Asp Ile Gln Val Val Ala Tyr

1135 TCC TCC TTC GGT CCT CAA TCA TTC ATT GAG ATG GAC TTA CAG 1176
     Ser Ser Phe Gly Pro Gln Ser Phe Ile Glu MET Asp Leu Gln

1177 TTG GCA AAA ACC ACG CCA ACT CTG TTC GAG AAT GAT GTA ATC 1218
     Leu Ala Lys Thr Thr Pro Thr Leu Phe Glu Asn Asp Val Ile

1219 AAG AAG GTC TCA CAA AAC CAT CCA GGC AGT ACC ACT TCC CAA 1260
     Lys Lys Val Ser Gln Asn His Pro Gly Ser Thr Thr Ser Gln

1261 GTA TTG CTT AGA TGG GCA ACT CAG AGA GGC ATT GCC GTC ATT 1302
     Val Leu Leu Arg Trp Ala Thr Gln Arg Gly Ile Ala Val Ile

1303 CCA AAA TCT TCC AAG AAG GAA AGG TTA CTT GGC AAC CTA GAA 1344
     Pro Lys Ser Ser Lys Lys Glu Arg Leu Leu Gly Asn Leu Glu

1345 ATC GAA AAA AAG TTC ACT TTA ACG GAG CAA GAA TTG AAG GAT 1386
     Ile Glu Lys Lys Phe Thr Leu Thr Glu Gln Glu Leu Lys Asp

1387 ATT TCT GCA CTA AAT GCC AAC ATC AGA TTT AAT GAT CCA TGG 1428
     Ile Ser Ala Leu Asn Ala Asn Ile Arg Phe Asn Asp Pro Trp

1429 ACC TGG TTG GAT GGT AAA TTC CCC ACT TTT GCC TGA TCC AGC 1470
     Thr Trp Leu Asp Gly Lys Phe Pro Thr Phe Ala TER       (SEQ ID NO:29)

HindIII
     GATCAAGCTT
                 AAT CCA TAC TCA ACG ACG ATA TG << 2nd left primer (SEQ ID NO:27)
1471 CAG TAA AAT CCA TAC TCA ACG ACG ATA TGA ACA AAT TTC CCT 1512

1513 CAT TCC GAT GCT GTA TAT GTG TAT AAA TTT TTA CAT GCT CTT 1554

1555 CTG TTT AGA CAC AGA ACA GCT TTA AAT AAA ATG TTG GAT ATA 1596
```

FIG. 2B

1597 CTT TTT CTG CCT GTG GTG TCA TCC ACG CTT TTA ATT CAT CTC 1638

1639 TTG TAT GGT TGA CAA TTT GGC TAT TTT TTA ACA GAA CCC AAC 1680

1681 GGT AAT TGA AAT TAA AAG GGA AAC GAG TGG GGG CGA TGA GTG 1722

1723 AGT GAT ACT AAA ATA GAC ACC AAG AGA GCA AAG CGG TCC AA 1764

1765 AAT CAT TTG AGT AAC CGG ATA TCT ATC GGG ATA TTA ATA GCA 1806

1807 GCT TCC ATT TCA ACT AAA ACA ACA GCA AGA TAT GAG CGA CAA 1848
                                                    MET Ser Asp Lys    (SEQ ID NO:30)
        2nd right primer  >>  GT TGT CGT TCT ATA CTC GCT G
                                                                      CCTAGGCATG (SEQ ID NO:28)
                                                                               BamHI

1849 GAT ATC CTT TCT ACC TCC CGA ACC CAT CCA ACT ACT TGA CGA 1890

1891 AGA CTC CAC GGA GCC TGA ACT CGA CAT TGA    1920    (SEQ ID NO:2)

FIG. 2C

GENETICALLY ENGINEERED YEAST AND MUTANTS THEREOF FOR THE EFFICIENT FERMENTATION OF LIGNOCELLULOSE HYDROLYSATES

CROSS-REFERENCE TO RELATED APPLICATIONS

This application is based on, and claims the benefit of the filing date of, U.S. Provisional Patent Application 60/082, 334, filed Apr. 20, 1998, the disclosure of which is relied upon and incorporated herein by reference in its entirety.

BACKGROUND OF THE INVENTION

1. Field of the Invention

This invention relates to recombinant integration vectors. More specifically, this invention provides recombinant integration vectors containing sequences of a gene encoding an aldose reductase (AR), but not the entire AR gene. The recombinant vector can be used to specifically delete or disrupt the AR-encoding gene of a host cell. The recombinant vector also permits any heterologous sequence to be integrated into the host genomic AR sequence. Integration into the AR sequence of, for example a yeast strain, renders the recombinant strain less efficient at producing, or even unable to produce, xylitol from xylose. The recombinant vector can further be used to insert genes coding for xylose utilizing enzymes, which provides a recombinant strain which not only can utilize xylose but is simultaneously prevented from xylitol formation through the action of the AR.

2. Description of the Related Art

Lignocellulose is the main component of forest product residues and agricultural waste. Lignocellulosic raw materials are mainly composed of cellulose, hemicellulose, and lignin. The cellulose fraction is made up of glucose polymers, whereas the hemicellulose fraction is made up of a mixture of glucose, galactose, mannose, xylose, and arabinose polymers. The lignin fraction is a polymer of phenolic compounds.

The cellulose and hemicellulose fractions can be hydrolyzed to monomeric sugars, which can be fermented to ethanol. Ethanol can serve as an environmentally friendly liquid fuel for transportation, since carbon dioxide released in the fermentation and combustion processes will be taken up by growing plants in forests and fields.

The price for lignocellulose-derived ethanol has been estimated by von Sivers et al. ("Cost analysis of ethanol production from willow using recombinant *Escherichia coli*", *Biotechnol. Prog.* 10:555–560, 1994). The calculations are based on the fermentation of all hexose sugars (glucose, galactose, and mannose) to ethanol. It was estimated that the fermentation of pentose sugars (xylose and arabinose) to ethanol will reduce the price of ethanol by approximately 25%. Xylose is found in hardwood hemicellulose, whereas arabinose is a component in hemicellulose in certain agricultural crops, such as corn. In order to make the price more competitive, the price must be reduced.

The release of monomeric sugars from lignocellulosic raw materials also releases by-products, such as weak acids, furans, and phenolic compounds, which are inhibitory to the fermentation process. Numerous studies have shown that the commonly used Baker's yeast, *Saccharomyces cerevisiae*, is the only ethanol producing microorganism that is capable of efficiently fermenting non-detoxified lignocellulose hydrolysates (Olsson and Hahn-Hägerdal, "Fermentation of lignocellulosic hydrolysates for ethanol production", *Enzyme Microbial Technol.* 18:312–331, 1996). Particularly efficient fermenting strains of *S. cerevisiae* have been isolated from the fermentation plant at a pulp and paper mill (Linden et al., "Isolation and characterization of acetic acid-tolerant galactose-fermenting strains of *Saccharomyces cerevisiae* from a spent sulfite liquor fermentation plant", *Appl. Environ.Microbiol.*58:1661–1669, 1992).

*S. cerevisiae* ferments the hexose sugars glucose, galactose and mannose, but is unable to ferment the pentose sugars xylose and arabinose due to the lack of one or more enzymatic steps. *S. cerevisiae* can ferment xylulose, an isomerization product of xylose, to ethanol (Wang et al., "Fermentation of a pentose by yeasts", *Biochem. Biophys. Res. Commun.* 94:248–254,1980; Chiang et al., "D-Xylulose fermentation to ethanol by *Saccharomyces cerevisiae*", *Appl. Environ. Microbiol.* 42:284–289,1981; Senac and Hahn-Hägerdal, "Intermediary metabolite concentrations in xylulose- and glucose-fermenting *Saccharomyces cerevisiae* cells", *Appl. Environ. Microbiol.* 56:120–126, 1990).

In eukaryotic cells, the initial metabolism of xylose is catalyzed by a xylose reductase (XR), which reduces xylose to xylitol, and a xylitol dehydrogenase (XDH), which oxidizes xylitol to xylulose. Xylulose is phosphorylated to xylulose 5-phosphate by a xylulose kinase (XK) and further metabolized through the pentose phosphate pathway and glycolysis to ethanol.

*S. cerevisiae* has been genetically engineered to metabolize and ferment xylose. The genes for XR and XDH from the xylose fermenting yeast *Pichia stipitis* have been expressed in *S. cerevisiae* (European Patent to C. Hollenberg, 1991; Hallborn et al., "Recombinant yeasts containing the DNA sequences coding for xylose reductase and xylitol dehydrogenase enzymes", WO91/15588; Kötter and Ciriacy, "Xylose fermentation by *Saccharomyces cerevisiae*", *Appl. Microbiol. Biotechnol.* 38:776–783, 1993). The transformants metabolize xylose but do not ferment the pentose sugar to ;ethanol.

When the gene for the enzyme transaldolase (TAL) is overexpressed in xylose- metabolizing transformants, the new recombinant strains grow better on xylose but still do not produce any ethanol from xylose (Walfridsson et al., "Xylose-metabolizing *Saccharomyces cerevisiae* strains overexpressing the TKL1 and TAL1genes encoding the pentose phosphate pathway enzymes transketolase and transaldolase", *Appl. Environ. Microbiol.* 61:4184–4190, 1995). In these strains, the major metabolic by-product, in addition to cell mass, is xylitol formed from xylose through the action of the enzyme XR. When the expression of XDH is ten times higher than the expression of XR, xylitol formation is reduced to zero (Walfridsson et al., "Expression of different levels of enzymes from *Pichia stipitis* XYL1 and XYL2 genes in s and its effect on product formation during xylose utilization", *Appl. Microbiol. Biotechnol.* 48:218–224, 1997). However, xylose is still not fermented to ethanol.

The gene for xylulose kinase (XK) from *S. cerevisiae* has been cloned and overexpressed in XR-XDH-expressing transformants of *S. cerevisiae* (Deng and Ho, "Xylulokinase activity in various yeasts including *Saccharomyces cerevisiae* containing the cloned xylulokinase gene", *Appl. Biochem. Biotechnol.* 24/25:193–199, 1990; Ho and Tsao, "Recombinant yeasts for effective fermentation of glucose and xylose", WO95/13362, 1995; Moniruzzaman et al., "Fermentation of corn fibre sugars by an engineered xylose utilizing Saccharomyces strain", *World J. Microbiol. Biotechnol.* 13:341–346,1997). These strains have been shown to produce net quantities of ethanol in fermentations of mixtures of xylose and glucose. Using the well established ribosomal integration protocol, the genes have been chromosomally integrated to generate strains that can be used in complex media without selection pressure (Ho and Chen, "Stable recombinant yeasts for fermenting xylose to ethanol", WO97/42307; Toon et al., "Enhanced cofermentation of glucose and xylose by recombinant Saccharomyces yeast strains in batch and continuous operating modes", *Appl. Biochem. Biotechnol.* 63/65:243–255, 1997).

In prokaryotic cells, xylose is isomerized to xylulose by a xylose isomerase (Xl). Xylulose is further metabolized in the same manner as in the eukaryotic cells. Xl from the thermophilic bacterium *Thermus thermophilus* was expressed in *S. cerevisiae*, and the recombinant strain fermented xylose to ethanol (Walfridsson et al., "Ethanolic fermentation of xylose with *Saccharomyces cerevisiae* harboring the *Thermus thermophilus* xylA gene which expresses an active xylose (glucose) isomerase", *Appl. Environ. Microbiol.* 62:4648–4651, 1996). The low level of ethanol produced was assumed to be due to the fact that the temperature optimum of the enzyme is 85° C., whereas the optimum temperature for a yeast fermentation is 30° C.

Recently, the gene for Xl from a mesophilic bacterium, *Streptomyces diastaticus*, has been cloned and transformed into *S. cerevisiae*. When xylose is fermented by an Xl expressing transformant of *S. cerevisiae*, a considerable amount of xylitol is formed in addition to ethanol. The xylitol is believed to be produced by an unspecified aldose reductase (AR) (Kuhn et al., "Purification of an aldo-keto reductase from *Saccharomyces cerevisiae*", *Appl. Environ. Microbiol.* 61:1580–1585, 1995).

Although great strides have been made, there exists a need in the art for a method of efficiently fermenting lignocellulose hydrolysates to produce ethanol.

SUMMARY OF THE INVENTION

In order fulfill the above-noted need, the present invention provides genetically engineered (recombinant) expression vectors, and recombinant cells capable of fermenting lignocellulose hydrolysates to ethanol. This invention aids in fulfilling a need in the art by providing integration vectors containing sequences of an aldose reductase (AR). The recombinant vectors can be used to specifically delete or disrupt an endogenous AR gene, and can also be used to incorporate heterologous polynucleotide sequences into host (recipient) cells. The recombinant vector constructs permit any gene, including those coding for xylose-utilizing enzymes, to be integrated in the AR gene sequence. In this way, recombinant cells are produced that show enhanced conversion of xylose to ethanol while simultaneously showing reduced xylitol formation through the action of the endogenous AR.

Accordingly, the invention provides methods of making recombinant cells and methods of efficiently producing ethanol from lignocellulose-containing compositions.

BRIEF DESCRIPTION OF THE DRAWINGS

This invention will be described in greater detail with reference to the drawings in which:

FIG. 2 depicts SEQ ID NO:1 (the nucleotide sequence of the gene encoding aldose reductase (AR) of *S. cerevisiae* and flanking sequences), SEQ ID NO:29 (the deduced amino acid sequence of the AR), and the location and sequence of PCR primers (SEQ ID NOS:25–28) used to amplify flanking sequences of the invention in the Examples.

DETAILED DESCRIPTION OF THE INVENTION

Figure 1:
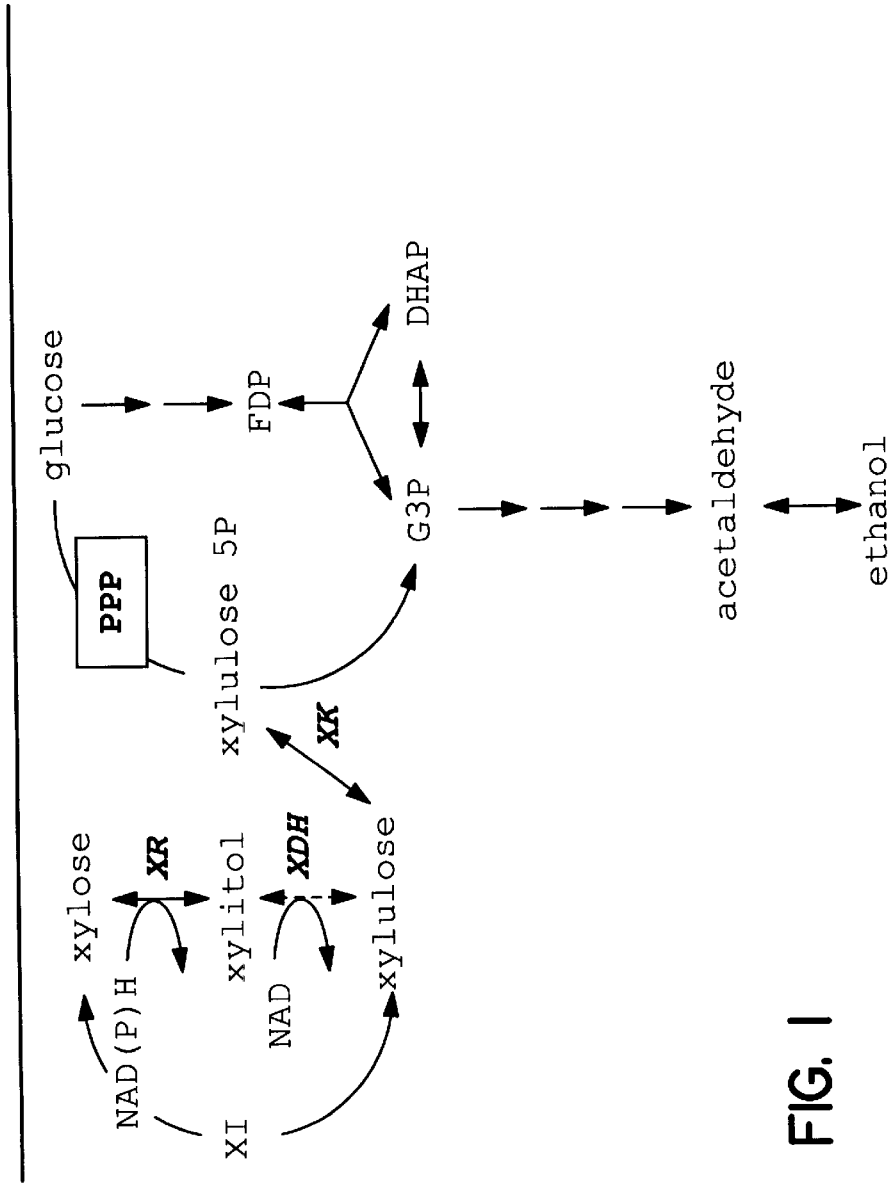
FIG. 1 depicts a metabolic scheme for the fermentation of lignocellulose hydrolysates.

The present invention provides a recombinant vector that can be used to transfer genetic information to a host cell. The recombinant vector includes, as a base molecule a vector known in the genetic engineering (molecular biology) art, including, but not necessarily limited to, a shuttle vector, an expression vector, a cloning (including subcloning) vector, and an integration vector. As used herein, "vector" refers to polynucleotide molecules that can be used to accept, donate, transfer, and/or maintain non-homologous (heterologous) polynucleotide sequences, while a "recombinant vector" according to the invention includes not only a "vector", but heterologous sequences as well. Examples of vectors include, but are not limited to, plasmids, phages or other viruses (including phage and other viral genomes existing independent of an intact virus particle), cosmids, phagemids, and yeast artificial chromosomes (YACs). Preferably, the vector contains all of the sequences necessary for its intended purpose. For example, if it is intended as a long-term expression vector, it preferably contains an origin of replication that is functional in the host cell. Further, if it is intended as an expression vector (i.e., the base molecule for a recombinant vector), it preferably contains expression controlling sequences (e.g., promoter, enhancer, etc.) operably linked to the sequence which is to be expressed.

Preferred vectors of the invention can comprise, or comprise portions of, a member selected from the group consisting of pUC19, pMA91, pBR322, Ylplac vectors, YEplac vectors, YBplac vectors, and pBluescript vectors. Other preferred vectors are discussed further herein.

The recombinant vector of the invention contains sequences of a gene encoding an aldose reductase (AR), or a related sequence. Preferably, the sequences are flanking sequences taken from one or both ends of the AR-encoding gene. As used hereinafter, "flanking sequence" encompasses any sequence from the AR-encoding gene, but not the entire gene sequence. A flanking sequence is not limited to those sequences at, or near, the termini of the gene. The flanking or flanking-related sequence can be used as a target sequence for not only deleting an endogenous AR-encoding sequence from a host cell, but for subcloning of any desired polynucleotide sequence into the recombinant vector, and preferably into a host cell as well. The AR flanking sequences can be those of any AR-encoding gene known. Preferably, the AR flanking sequences are those of a yeast. More preferably, the flanking sequences are those of the AR-encoding gene of *Saccharomyces cerevisiae*, or a related sequence. In a highly preferred embodiment, the flanking sequences comprise sequences found within the sequence of SEQ ID NO:1, or its complementary sequence. The flanking sequences, or sequence related thereto, need not be localized from either end of the sequence of SEQ ID NO:1, but can be any useful sequence(s) selected therefrom.

For example, two flanking sequences, the first comprising nucleotides 50–470 and the second comprising nucleotides 1477–1846, of SEQ ID NO:1 can be used in a vector according to the invention. These sequences can be chemically synthesized de novo using SEQ ID NO:1 as a guide or can be amplified in vitro from SEQ ID NO:1 using known techniques. It is preferred that the sequences be amplified from SEQ ID NO:1 in vitro using known techniques, such as PCR. In this way, primers can be used which have been engineered to contain restriction endonuclease cleavage sites that are not naturally present in SEQ ID NO:1. Incorporation of such cleavage sites aids in subcloning of the amplified flanking sequence into the base vector (e.g., into pUC19). Other modifications to the sequence of SEQ ID NO:1 can be made as well, as long as the sequence falls within the definition of a related sequences as defined herein.

Other flanking sequence pairs can be chosen, such as: a pair wherein the first flanking sequence comprises nucleotides 1–126 and the second comprises nucleotides 1639–1814, of SEQ ID NO: 1; a pair wherein the first flanking sequence comprises nucleotides 476–990 and the second comprises nucleotides 1600–1920, of SEQ ID NO: 1; and a pair wherein the first flanking sequence comprises nucleotides 191–250 and the second comprises nucleotides 1380–1660, of SEQ ID NO:1. As mentioned above, each of flanking sequences preferably contains a restriction endonuclease cleavage site. If a convenient site does not exist in the sequence to be amplified, it can be engineered by incorporation into the primers that are used to amplify the sequence. Preferably the restriction endonuclease cleavage site is unique with respect to the flanking sequences to facilitate subcloning of the amplified sequences into the base vector molecule.

In other preferred embodiments, the sequences are related to the sequence of SEQ ID NO:1, or a fragment thereof. The related sequences can be sequences that hybridize to at least a portion of SEQ ID NO:1 under stringent conditions. As used herein, stringent conditions are in vitro hybridization conditions in which two polynucleotide molecules are in a substantially hybridized state in the presence of 5XSSPE, 2XDenhardt's solution, and 0.5% (w/v) sodium dodecyl sulfate after at least 20 minutes at 65° C. More stringent conditions are those where the percentage of molecules that are in a hybridized state is lower than the percentage under the above-noted conditions. Such conditions are well-known to the ordinary artisan, and can include a temperature above 65° C. and/or a lower ionic strength solution. By "substantially hybridized state" it is meant that, while not all molecules present that are capable of hybridizing are actually hybridized, enough molecules are found in the hybridized state that hybridized, double-stranded polynucleotide complexes can be detected in a reasonable amount of time using techniques known to the skilled artisan. The length of contiguously hybridized nucleotides is not absolutely critical, nor is the percent identity between the two hybridizing molecules. Rather, it is the combination of these two physical characteristics, among other physical characteristics, that determines which molecules are included within the invention. Such molecules can easily be determined by those of ordinary skill in the art using well-known and widely-practiced techniques.

However, related sequences according to the invention can be characterized in terms of their percent identity with SEQ ID NO:1, or fragments of SEQ ID NO:1. In preferred embodiments of this aspect of the invention, the sequences are sequences that show at least 50% identity to at least a portion of SEQ ID NO:1. For example, polynucleotide molecules having 50% identity with SEQ ID NO:1 or a fragment of SEQ ID NO:1 are within the present invention. It is preferred that a polynucleotide molecule according to this aspect of the invention have at least 75%, and more preferably at least 85% identity with SEQ ID NO:1 or a fragment of SEQ ID NO:1. In highly preferred embodiments, a polynucleotide molecule according to this aspect of the invention has at least 90% identity with SEQ ID NO:1 or a fragment of SEQ ID NO:1, such as 95%, 98%, or approximately 99% or more.

Preferably, the fragment of SEQ ID NO:1 comprises at least 10 contiguous nucleotides of SEQ ID NO:1. More preferably, the fragment comprises at least 25, and more preferably, at least 50, contiguous nucleotides of SEQ ID NO:1. In highly preferred embodiments of the invention, the fragment comprises approximately 100 contiguous nucleotides of SEQ ID NO:1. Other embodiments include fragments having at least 100 contiguous nucleotides, such as approximately 150, 200, 300, and 500 contiguous nucleotides.

According to this aspect of the invention, percent identity is calculated using the BLAST sequence analysis program suite, Version 2, available at the NCBI (NIH). All default parameters are used. BLAST (Basic Local Alignment Search Tool) is the heuristic search algorithm employed by the programs blastp, blastn, blastx, tblastn, and tblastx, all of which are available through the BLAST analysis software suite at the NCBI. These programs ascribe significance to their findings using the statistical methods of Karlin and Altschul (1990, 1993) with a few enhancements. Using this publicly available sequence analysis program suite, the skilled artisan can easily identify polynucleotides according to the present invention.

When the flanking sequences are chosen from a sequence of SEQ ID NO:1, it is preferable that the sequences comprise at least 10 contiguous nucleotides from SEQ ID NO:1. In highly preferred embodiments, the flanking sequences comprise at least 25 contiguous nucleotides of SEQ ID NO:1. In other highly preferred embodiments, the flanking sequences comprise at least 50, and more preferably, approximately 100 or even more contiguous nucleotides of SEQ ID NO:1.

The vectors of the invention can be used for multiple applications. In embodiments of the invention, the vectors are used to specifically delete the AR-encoding gene of a recipient cell. In preferred embodiments, the recipient cell is a yeast cell, such as an *S. cerevisiae* cell. Other yeasts are well-known to the artisan, and include, but are not limited to, *Schizosaccharomyces pombe, Pichia stipitis*, and *Pichia pastoris*. Although the vector of the invention can be used to delete the AR by multiple mechanisms, it is preferred that in vivo deletion of an endogenous AR occur via homologous recombination with the AR-specific or -related sequences present on the vector. That is, by introducing a transfer vector comprising the flanking sequences of a AR, devoid of the entire AR gene, through homologous recombination between the AR sequences on the vector and the endogenous AR-encoding sequences, the endogenous AR-encoding gene can be specifically deleted. As discussed further below, any recombinant strain created in such a way will be unable to metabolize lignocellulose to produce xylitol (or will at the very least have this ability reduced), and may be able to produce a greater quantity of ethanol as a result. This is especially important in the fermentation of lignocellulose by yeasts.

Other techniques for insertion of heterologous nucleic acid molecules into the genome of a recipient cell are known to the skilled artisan in the field. The skilled artisan is free to choose among these techniques to achieve incorporation of the heterologous sequences into the host genome. The choice will be based, at least in part, on the preference of the artisan, as well as the convenience and cost of the technique. For example, the heterologous sequence(s) of one vector construct according to the invention may be inserted into the host genome using homologous recombination via DNA strand crossing over whereas another heterologous sequence may be inserted using the ribosomal integration protocol. The technique used is not critical to the practice of the invention, and the ability to choose an appropriate technique and protocol is well within the abilities of the skilled artisan in the field.

Of course, specific deletion of the AR-encoding gene of an organism, such as a yeast, can occur simultaneously with the introduction of a new, heterologous sequence or multiple sequences. In essence, the AR-encoding gene is replaced by the new sequence(s), preferably by homologous recombination. By "heterologous" it is meant any sequence that is not identical to the gene being replaced. That is, the heterologous sequence can be an AR-encoding gene from another organism, a mutant form of the AR-encoding gene of the host cell, a gene not known to be related in structure or function to the AR-encoding gene of the host cell, or any other sequence that is not identical to the endogenous host cell gene.

In embodiments where a heterologous sequence is present on the recombinant vector of the invention, the heterologous sequence can be inserted into the recombinant vector using any method known to the skilled artisan. For example, the heterologous sequence can be inserted in the vector using restriction endonuclease cleavage/re-ligation techniques or via homologous recombination. Preferably, the heterologous sequence is inserted between two flanking sequences of the AR-encoding gene, or between two AR-related sequences such that, upon introduction into the recipient cell, homologous recombination can occur, resulting in incorporation of the heterologous sequence into the genome of the recipient cell. Further, the heterologous sequence can be generated from multiple different source nucleic acids, or from in vitro amplification of a single or multiple source sequences (e.g., using PCR). The heterologous sequence need not encode a structural protein, but can comprise regulatory elements alone or in combination with a structural gene. The heterologous sequence can also comprise nucleotide sequences with no known function.

In a preferred aspect of the invention, multiple heterologous sequences are inserted between two AR-flanking or -related sequences. In this aspect of the invention, multiple genes can be inserted in place of the AR-encoding gene being deleted. This permits the artisan practicing the invention to modify the genome of the recipient (recombinant) cell such that a naturally-occurring metabolic pathway is shut down while, at the same time, another metabolic pathway can be created or enhanced. According to this aspect of the invention, multiple copies of each of the heterologous sequences can be inserted into the host genome using the vector of the invention. Accordingly, multiple copies of a certain sequence can be included in the recombinant vector of the invention while multiple or single copies of other sequences are included as well. In this way, the expression of all of the genes of a construct can be regulated, broadly or specifically, in respect to each other. Techniques for manipulating nucleic acids in accordance with this invention are well-known and widely-practiced by the skilled artisan.

For example, a recombinant vector according to the present invention can comprise the xylose isomerase (Xl) gene (XylA) from *Thermus thermophilus* (Dekker et al., "Xylose (glucose) isomerase gene from the thermophile *Thermus thermophilus*: cloning, sequencing, and comparison with other thermostable xylose isomerases", *J. Bacteriol.* 173(10):3078–3083, 1991; GenBank Accession No. D90256) inserted between two flanking sequences. A recombinant vector according to the invention can comprise the gene encoding Xl from *Streptomyces diastaticus* inserted between two flanking sequences. Furthermore, a recombinant vector according to the invention can comprise both the gene encoding Xl from *T. thermophilus* and the gene encoding Xl from *S. diastaticus*, in any ratio and order. Other exemplary recombinant vectors can comprise at least one XI-encoding gene and at least one XK-encoding gene (XK). There can be the same number of copies of each gene within the recombinant vector, or different numbers of copies. Additionally, an XK-encoding gene can be isolated from any known source (e.g., from *S. cerevisiae* or *P. stipitis*) and incorporated into a recombinant vector of the invention. Again, multiple heterologous sequences can be present on a single recombinant vector; therefore, the XK-encoding gene, in any copy number, can be incorporated into a recombinant vector comprising an XI-encoding gene, in any copy number.

In preferred embodiments of the invention, the heterologous sequences are coding sequences for enzymes involved in hemicellulose metabolism. It is preferable that these coding sequences encode enzymes involved in the metabolism of hemicellulose to ethanol. Thus, the coding sequences that are inserted into the recombinant vectors of the invention preferably encode enzymes such as Xl (encoded by XYlA), XK (encoded by XK and XKS1), XDH (encoded by XYL2), and XR (encoded by XYL1). Other genes that may be included in the recombinant vectors are TAL1 (encoding transaldolase), TKL1 (encoding transketolase), pntA and pntB (encoding nicotinamide nucleotide transhydrogenase), and cth (encoding transhdrogenase). The nucleotide sequences of representatives of each of these genes are publicly available without restriction.

Many of the nucleotide sequences of the genes encoding heterologous enzymes involved in production of ethanol from xylose are known and publicly available. Using well-known and widely practiced molecular biology techniques (e.g., restriction endonuclease cleavage/re-ligation, PCR, etc.), these sequences, or portions of these sequences, can be subcloned between the flanking sequences of the recombinant vectors of the present invention. Many techniques for subcloning heterologous sequences are known to the skilled artisan. Any suitable technique can be used as long as the technique results in a recombinant vector that can function according to the invention. Where convenient restriction endonuclease cleavage sites are not present in the heterologous sequences, site-directed mutagenesis, and/or mismatches in the primers can be used to engineer such sites prior to subcloning the heterologous sequences into the recombinant vectors of the invention. Such genetic engineering techniques are well within the ordinary artisan's knowledge and abilities, and can be performed without undue or excessive experimentation.

The recombinant vector of the invention can be used to genetically engineer a host cell. Thus, the present invention provides recombinant cells comprising the vector of the invention. The recombinant vector can be maintained within the host cell as an autonomously-replicating molecule, or a portion of the recombinant vector can be incorporated in the genome of the host. Thus, because the recombinant vector of the invention can be an integration vector, the present invention provides recombinant hosts comprising that portion of the recombinant vector which has been integrated into the host cell genome.

In one embodiment of this aspect of the invention, at least a portion of the recombinant vector is integrated into the host genome. In this embodiment, the recombinant cells of the invention have at least one copy of an endogenous AR-encoding gene disrupted or deleted by insertion of sequences of the recombinant vector into the genome. Many of the advantages of the invention are realized through the disruption and/or deletion of a host cell's endogenous AR-encoding gene.

For example, disruption and/or deletion of a gene encoding AR reduces or eliminates the recombinant cell's ability to convert xylose to xylitol. As can be seen from FIG. 1, when XR (xylose reductase—an aldose reductase) function is disrupted, direct conversion of xylose to xylitol is blocked, forcing the metabolic degradation of xylose to flow through xylulose. Although it is apparent that xylulose can be converted to xylitol via the XDH, it is also apparent that a greater amount of ethanol is produced from xylose when the AR (XR) is inactive because there is a single pathway leading to xylitol (xylulose to xylitol) instead of two pathways (xylulose to xylitol and xylose to xylitol).

In addition, in embodiments where at least one heterologous sequence is inserted between the AR flanking sequences in the recombinant vector, increased production of xylose-metabolizing enzymes can be effected. For example, the recombinant vector of the invention can comprise one or several copies of an XK-encoding gene inserted between the AR flanking sequences. When this recombinant vector is introduced into a host cell, a recombinant cell according to the invention is achieved, and this recombinant cell comprises not only a non-functional AR-encoding gene, but at least one additional copy of an XK-encoding gene. Upon expression, the recombinant cell will produce increased amounts of XK, thus increasing the relative amount of xylulose converted to xylulose-5-phosphate (relative to the amount of xylulose converted to xylitol).

As discussed above, the recombinant vectors of the invention can contain multiple copies of any number of genes involved in xylose metabolism, and especially xylose conversion to ethanol. Thus, in addition to containing at least one copy of an XK-encoding gene, the recombinant vector can also contain at least one copy of any of the genes encoding enzymes of the Embden-Meyerhof-Parnas pathway or other enzymes necessary for conversion of glucose to ethanol in yeasts. Such enzymes include, but are not necessarily limited to, glyceraldehyde-3-phosphate dehydrogenase, 3-phosphoglycerate kinase, phosphoglycerate mutase, enolase, pyruvate kinase, pyruvate decarboxylase, and alcohol dehydrogenase. By supplying copies of genes encoding these enzymes, conversion of xylose to ethanol can be improved to an even greater degree. This is because the increased number of ethanol-specific enzymes will permit the recombinant cell to rapidly utilize any xylulose-5-phosphate present. By rapidly depleting the xylulose-5-phosphate, and maintaining a very low level of it, the amount of xylitol produced from xylulose will be substantially decreased because rapid production and subsequent consumption of xylulose-5-phosphate will diminish the amount of xylulose available for conversion to xylitol.

Thus, the recombinant cells of the invention provide a solution to the need in the art for increased production, at economical rates, of ethanol from compositions comprising lignocellulose and its hydrolysates. Although the recombinant cells of the invention find their most highly valued use in industrial settings, they can also be utilized as research tools and as basic materials for further recombinant manipulation. Furthermore, although the above discussion is focused on recombinant yeast cells, the recombinant cells are not limited to such cells. Rather, any cell comprising an AR-encoding gene is encompassed by this invention.

Accordingly, the invention provides a method of making recombinant cells. The method comprises providing a recombinant vector according to the invention and inserting that vector into a host cell to create a recombinant cell. The method can optionally include culturing the recombinant cell under conditions where the heterologous sequences present on the recombinant vector are expressed. The method can also optionally include maintaining the recombinant cell under conditions where integration of at least a portion of the recombinant vector into the host genome occurs. Furthermore, the method can optionally include storing the recombinant cells in an environment where the cell remains viable and stable for extended periods of time (e.g., frozen or lyophilized). Conditions under which these optional method steps can be performed are well-known and widely practiced skilled artisan.

Suitable host cells include any prokaryotic and eukaryotic cells having an AR-encoding gene. In preferred embodiments of the invention, the host cell is a yeast, especially a yeast of the Saccharomyces family. Exemplary host cells include CEN.PK (pgi6), CEN.PK (pgi7), isolate 3 of Linden et al., 1992, and isolate 10 of Linden et al., 1992.

In addition, the invention provides a method of degrading lignocellulose-containing compositions and compositions containing lignocellulose hydrolysates. The method comprises combining at least one recombinant cell of the invention with the lignocellulose-containing composition and incubating the mixture under conditions that permit degradation of the lignocellulose or other components present in the composition.

Preferably, the method is used as a method of producing ethanol from lignocellulose-containing compositions and compositions comprising lignocellulose hydrolysates. The method can be a method of fermenting lignocellulose or lignocellulose hydrolysates, and provides the production of relatively high levels of ethanol and relatively low levels of xylitol. The method of producing ethanol comprises the following steps:

(a) providing a composition containing lignocellulose or a hydrolysate or metabolic degradation product of lignocellulose, (b) providing a recombinant cell according to the invention, (c) combining the recombinant cell of the invention with the composition containing lignocellulose or a hydrolysate or metabolic degradation product of lignocellulose, (d) allowing the recombinant strain to metabolize the lignocellulose or breakdown product, and (e) harvesting or purifying the metabolic products produced by the breakdown of the lignocellulose or hydrolysate.

Preferably, the method results in production of ethanol. In this situation, the method optionally further includes purifying or isolating the ethanol from other components present in the mixture formed by the combination of the recombinant cell and the composition comprising lignocellulose or its hydrolysates. The method of producing ethanol provides high levels of ethanol production, and low levels of xylitol production from lignocellulose-containing compositions, especially those in which xylose is found. The amount of ethanol produced from lignocellulose-containing compositions or lignocellulose hydrolysate-containing compositions is much greater than the amount that can be produced from lignocellulose- or lignocellulose hydrolysate-degrading strains currently available.

It is highly preferable that the conditions under which the recombinant strain is allowed to metabolize or degrade components of the composition include anaerobic conditions; however, pseudo-anaerobic conditions are also preferred while aerobic conditions are acceptable.

The recombinant strains of the invention are useful for the efficient fermentation of lignocellulose hydrolysates.

EXAMPLES

Example 1

Amplification of the xylA gene from *Thermus thermophilus* and construction of plasmid pBX1

Two primers were used to amplify the xylA gene using PCR amplification:

5'-GCGCTGATCATCTAGAATGTACGAGC-CCAAACCGGAGCACAG-3'(SEQ ID NO:2; 5' primer) and

5'-GCTTTGATCATCTAGATCACCCCCGCAC-CCCCAGGAGGTACT-3' (SEQ ID NO:3; 3' primer).

Both primers contained restriction endonuclease sites for Bc/I and XbaI. The PCR mixture contained: PCR buffer with 2 mM $MgSO_4$, 0.8 mM dNTPs, 0.3$\mu$M of each primer, 0.2 $\mu$g template (pUC19-XI), and 2.5 units Pwo DNA polymerase (Boehringer Mannheim).

A DNA Thermal Cycler (Perkin Elmer Cetus) was used for amplification of the gene under the following conditions: melting temperature 94° C. (1 min), annealing temperature 58° C. (1 min), and polymerization temperature 72° C. (1 min). Twenty-eight cycles were run with a subsequent polymerization period of 7 min at 72° C. The amplified DNA fragment was digested with BclI and ligated into the BglII site of pMA91, resulting in plasmid pBX1. The BglII site of pMA91 was placed between the phosphoglycerate kinase (PGK1) promoter and terminator.

Example 2

Amplification of the XYL1 gene of *P. stipitis* and creation of plasmid UA 103

Two primers were used to amplify the XYL1 gene from *P. stipitis* using PCR:

5'-GCGGATCCTCTAGAATGCGTTCTATTAAGTTGMCTCTGG-3' (5' primer; SEQ ID NO:4), and

5'-TTGGATCCTCTAGATTAGACGAAGATAG-GAATCTTGTCCC-3' (3' primer; SEQ ID NO:5).

The primers contained BamHI and XbaI restriction sites at both ends. PCR was performed as in Example 1. The PCR amplified chromosomal region was cut with BamHI and subcloned into the BglII site of the yeast expression vector pMA91 between the PGK promoter and terminator, giving the plasmid pUAI103.

Example 3

Amplification of the XYL1 and XYL2 genes of *P. stipitis*

Plasmids comprising the XYL1 and XYL2 genes of *P. stiptis* (pMW103 and pMW104, respectively; Walfridsson et al, 1995) were used to amplify the XYL1 and XYL2 genes using the following primers:

5'-CGCAGGATCCACTAGAATGCCTTCTAT-3' (SEQ ID NO:6)

5'-TCCTCTAGATTGGACGAAGATAGGAAT-3' (SEQ ID NO:7)

5'-GCGTCTAGAATGACTGCTAACCCTTCC-3' (SEQ ID NO:8)

5'-GCGCGAAGCTTAGATCTTTACTCAGGGCCGTCAA-3' (SEQ ID NO:9)

5'-GCCTCTAGAATGCCTTTATTAAG-3' (SEQ ID NO:10)

5'-GCGCGAAGCTTGGATCCTTAGACGAAGATAGGAA-3' (SEQ ID NO:11)

5'-CGCAGGATCCACTAGAATGACTGCTAACCCTTC-3' (SEQ ID NO:12)

5'-TCCTCTAGAACCCTCAGGGCCGTCAATG-3' (SEQ ID NO:13)

5'-GCCTCTAGACCATCTCCAACCGCTAGCA

CTAACCAAATGCCTTCTATTAAGTTG-3' (SEQ ID NO:14).

SEQ ID NO:6 corresponds to the 5' end of the XYL1 gene. SEQ ID NO:7 corresponds to the 3' end of the XYL1 gene. The XYL1 gene was amplified by PCR from plasmid pMW103. The amplified DNA was then cleaved with BamHI and XbaI, and inserted into pUC19.

SEQ ID NO:8 corresponds to the 5' end of the XYL2 gene. SEQ ID NO:9 corresponds to the 3' end of the XYL2 gene. The XYL2 gene was amplified by PCR from plasmid pMW104. The amplified DNA was then cleaved with HindIII and XbaI, and inserted into pUC19. The digested amplified DNA was also inserted into the pUC19 derivative disclosed above, which contained the amplified XYL1 gene.

Example 4

Amplification of the pntA and pntB from *E. coli*

The pntA gene was amplified from *E. coli* using PCR and the following primers:

5'-GCGCGAGATCTTCTAGAATGCGAATTGGCATACCAAG-3' (SEQ ID NO:15)

5'-CGCGCAGATCTTCTAGATTAATTTTTGCGGAACATTTTC-3' (SEQ ID NO:16)

The pntB gene was amplified from *E. coli* using PCR and the following primers:

5'-GCGCGAGATCTAAAATGTCTGGAGGATTAGTTAC-3' (SEQ ID NO:17)

5'-CGCGCAGATCTTTACAGAGCTTTCAGGATTGC-3' (SEQ ID NO:18).

The amplified genes were digested with the appropriate restriction endonucleases and subcloned into PUC19 vectors, alone and in combination.

Example 5

Amplification and subcloning of the cth gene of *Azotobacter vinelandii*

The cth gene of *A. vinelandii*, encoding the transhydrogenase, was amplified by PCR using the following primers:

5'-GtnTA(C/T)M(C/T)TA(C/T)GA(C/T)GTnGTnGTnAT(A/C/T)-3' (SEQ ID NO:19)

5'-(A/G)TA(A/G)TT(A/G)AAnGTnGT(A/G)TT(A/T/G)AT(A/G)M(A/G)TA-3' (SEQ ID NO:20).

From the PCR reaction, a fragment of 1300 bp was obtained and subcloned into pUC18.

Example 6

Amplification of P. stipitis polyol dehydrogenase gene

The gene encoding polyol dehydrogenase was amplified from P. stipitis using PCR and the following primers:

5'-GGATCCAGATCTATGGACTACTCATACGCT-3' (SEQ ID NO:21)

5'-GGATCCAGATCTTTAAACTGTGGGTCGTAT-3' (SEQ ID NO:22)

The gene was amplified and subcloned into pUC18.

Example 7

Cloning the xylulose kinase gene from S. cerevisiae

The XK from S. cerevisiae was amplified and subcloned using PCR and the following primers:

5'-GCGGATCCTCTAGAATGGTTTGTTCAGTAATTCAG-3' (SEQ ID NO:23)

5'-AGATCTGGATCCTTAGATGAGAGTCTTTTCCAG-3' (SEQ ID NO:24).

Example 8

Amplification of AR flanking sequence

Two flanking sequences from SEQ ID NO:1 were amplified using PCR and the following primers:
Upstream flanking region:

5'-GATCGAATTCTTTGTAACTGTAATTTCACTCATGC-3' (SEQ ID NO:25;

corresponding to nucleotides 50–74 of SEQ ID NO:1, with an EcoRl site engineered at the 5' end of the primer), and

5'-GTACMGCTTTTTCCMTTTTCCTTTACGATTT-3' (SEQ ID NO:26;

complementary to nucleotides 470–448 of SEQ ID NO:1, with a Hindlll site engineered at the 5' end of the primer);
Downstream flanking region:

5'-GATCAAGCTTAATCCATACTCMCGACGATATG-3' (SEQ ID NO:27;

corresponding to nucleotides 1477–1499 of SEQ ID NO:1, with a Hindlll site engineered at the 5' end of the primer), and

5'-GTACGGATCCGTCGCTCATATCTTGCTGTTG-3' (SEQ ID NO:28;

complementary to nucleotides 1846–1826 of SEQ ID NO:1, with a BamHl site engineered at the 5' end of the primer).

The primers were used to amplify regions of SEQ ID NO:1 and insert convenient restriction endonuclease cleavage sites into the sequences to facilitate subcloning of the flanking sequences into the base vector molecule.

Example 9

Construction of plasmid pUSM1004

Using PCR and primers based on SEQ ID NO:1, flanking sequences were amplified and subcloned into base vector pBR322. The 3' flanking region was ligated between the Hindlll and BamHl sites in pBR322 to create plasmid pUSM1002. The 5' flanking region was then ligated between the Hindlll and EcoRl sites of pUSM1002 to create plasmid pUSM1004, which contained both a 5' flanking sequence and a 3' flanking sequence of the AR-encoding gene of S. cerevisiae.

Example 10

Construction of plasmid pUSM1006

Plasmid pUSM1004 from Example 9 was digested with BamHl and EcoRl to release the AR flanking sequences. The liberated BamHl/EcoRl fragment was subcloned into base shuttle vector pUC8+URA to give plasmid pUSM1006.

Example 11

Construction of recombinant strains YUSM1006, MATa and β

Plasmid pUSM1006 was transfected into yeast strain CEN.PK2-1C and CEN.PK2-1 D using standard techniques. Transfectants were cultured to permit integration of the vector into the host genome. Stable recombinant cells were obtained.

Example 12

Construction of recombinant strain YKTR101

The xylA and XK genes were subcloned into plasmid pUSM1006.

The resulting plasmid was transfected into yeast strain using standard techniques. Transfectants were cultured to permit integration of the vector into the host genome. Stable recombinant cells (YKTR101) were obtained having the xylA and XK genes integrated into the host genome.

The invention has been described in detail above with reference to preferred embodiments. However, it will be understood by the ordinary artisan that various modifications and variations can be made in the practice of the present invention without departing from the scope or spirit of the invention. All references cited herein are hereby incorporated by reference in their entirety.

What is claimed is:

1. A recombinant vector comprising at least two flanking sequences from SEQ ID NO:9 ,
   wherein said at least two flanking sequences are not contiguous with each other on SEQ ID NO: 1 and together do not encode an aldose reductase enzyme, and
   wherein one of said at least two flanking sequences from SEQ ID NO: 1 comprises nucleotides 50–470, nucleotides 1–126, nucleotides 476–990, or nucleotides 191-250 of SEQ ID NO: 1.

2. A recombinant vector comprising at least two flanking sequences from SEQ ID NO: 1,
   wherein said at least two flanking sequences are not contiguous with each other on SEQ ID NO: 1 and together do not encode an aldose reductase enzyme, and
   wherein one of said at least two flanking sequences from SEQ ID NO: 1 comprises nucleotides 1477–1846, nucleotides 1639–1814, nucleotides 1600–1920, or nucleotides 1380–1660 of SEQ ID NO:1.

3. A recombinant vector comprising at least two flanking sequences from SEQ ID NO:1,
   wherein said at least two flanking sequences are not contiguous with each other on SEQ ID NO: 1 and together do not encode an aldose reductase enzyme, and
   wherein one of said at least two flanking sequences from SEQ ID NO: 1 comprises nucleotides 50–470, nucleotides 1–126, nucleotides 476–990, or nucleotides 191–250 of SEQ ID NO: 1, and another of said at least two flanking sequences from SEQ ID NO: 1 comprises nucleotides 1477–1846, nucleotides 1639–1814, nucleotides 1600–1920, or nucleotides 1380–1660 of SEQ ID NO: 1.

4. Recombinant yeast strain YUSM1006MATa.
5. Recombinant yeast strain YUSM1006MATβ.
6. Recombinant yeast strain YKTR101.
7. Recombinant plasmid pUSM1004.
8. Recombinant plasmid pUSM1006.

* * * * *

UNITED STATES PATENT AND TRADEMARK OFFICE
CERTIFICATE OF CORRECTION

PATENT NO. : 6,410,302 B1  Page 1 of 1
DATED : June 25, 2002
INVENTOR(S) : K.L. Träff, R.R. Cordero Otero, W.H. Van Zyl and B. Hahn-Hägerdal It is certified that error appears in the above-identified patent and that said Letters Patent is hereby corrected as shown below:

Column 27,
Line 24, "SEQ ID NO:9 ," should read -- SEQ ID NO:1, --.

Column 28,
Line 38, "YUSM1006MAT$\beta$" should read -- YUSM1006MAT$\alpha$ --.

Signed and Sealed this

Twenty-second Day of October, 2002

Attest:

JAMES E. ROGAN
Attesting Officer          Director of the United States Patent and Trademark Office

SEQUENCE LISTING

<160> NUMBER OF SEQ ID NOS: 30

<210> SEQ ID NO 1
<211> LENGTH: 1920
<212> TYPE: DNA
<213> ORGANISM: Saccharomyces cerevisiae
<220> FEATURE:
<221> NAME/KEY: CDS
<222> LOCATION: (481)..(1461)
<220> FEATURE:
<221> NAME/KEY: CDS
<222> LOCATION: (1838)..(1849)

<400> SEQUENCE: 1

```
ccgtgttcat caagaaatgg gcgcattact acaagaagtt ttgatatttt ttgtaactgt      60
aatttcactc atgcacaaga aaaaaaaaac tggattaaaa gggagcccaa ggaaaactcc     120
tcagcatata tttagaagtc tcctcagcat atagttgttt gttttcttta cacattcact     180
gtttaataaa acttttataa tatttcatta tcggaactct agattctata cttgtttccc     240
aattgttgct ggtagtaaac gtatacgtca taaaagggaa aagccacatg cggaagaatt     300
ttatggaaaa aaaaaaaacc tcgaagttac tacttctagg gggcctatca agtaaattac     360
tcctggtaca ctgaagtata taagggatat agaagcaaat agttgtcagt gcaatccttc     420
aagacgattg ggaaaatact gtaatataaa tcgtaaagga aaattggaaa ttttttaaag     480 atg tct tca ctg gtt act ctt aat aac ggt ctg aaa atg ccc cta gtc      528
Met Ser Ser Leu Val Thr Leu Asn Asn Gly Leu Lys Met Pro Leu Val
  1               5                  10                  15 ggc tta ggg tgc tgg aaa att gac aaa aaa gtc tgt gcg aat caa att      576
Gly Leu Gly Cys Trp Lys Ile Asp Lys Lys Val Cys Ala Asn Gln Ile
             20                  25                  30 tat gaa gct atc aaa tta ggc tac cgt tta ttc gat ggt gct tgc gac      624
Tyr Glu Ala Ile Lys Leu Gly Tyr Arg Leu Phe Asp Gly Ala Cys Asp
         35                  40                  45 tac ggc aac gaa aag gaa gtt ggt gaa ggt atc agg aaa gcc atc tcc      672
Tyr Gly Asn Glu Lys Glu Val Gly Glu Gly Ile Arg Lys Ala Ile Ser
     50                  55                  60 gaa ggt ctt gtt tct aga aag gat ata ttt gtt gtt tca aag tta tgg      720
Glu Gly Leu Val Ser Arg Lys Asp Ile Phe Val Val Ser Lys Leu Trp
 65                  70                  75                  80 aac aat ttt cac cat cct gat cat gta aaa tta gct tta aag aag acc      768
Asn Asn Phe His His Pro Asp His Val Lys Leu Ala Leu Lys Lys Thr
                 85                  90                  95 tta agc gat atg gga ctt gat tat tta gac ctg tat tat att cac ttc      816
Leu Ser Asp Met Gly Leu Asp Tyr Leu Asp Leu Tyr Tyr Ile His Phe
            100                 105                 110 cca atc gcc ttc aaa tat gtt cca ttt gaa gag aaa tac cct cca gga      864
Pro Ile Ala Phe Lys Tyr Val Pro Phe Glu Glu Lys Tyr Pro Pro Gly
        115                 120                 125 ttc tat acg ggc gca gat gac gag aag aaa ggt cac atc acc gaa gca      912
Phe Tyr Thr Gly Ala Asp Asp Glu Lys Lys Gly His Ile Thr Glu Ala
    130                 135                 140 cat gta cca atc ata gat acg tac cgg gct ctg gaa gaa tgt gtt gat      960
His Val Pro Ile Ile Asp Thr Tyr Arg Ala Leu Glu Glu Cys Val Asp
145                 150                 155                 160 gaa ggc ttg att aag tct att ggt gtt tcc aac ttt cag gga agc ttg     1008
Glu Gly Leu Ile Lys Ser Ile Gly Val Ser Asn Phe Gln Gly Ser Leu
                165                 170                 175 att caa gat tta tta cgt ggt tgt aga atc aag ccc gtg gct ttg caa     1056
```

```
            Ile Gln Asp Leu Leu Arg Gly Cys Arg Ile Lys Pro Val Ala Leu Gln
                    180                 185                 190 att gaa cac cat cct tat ttg act caa gaa cac cta gtt gag ttt tgt         1104
Ile Glu His His Pro Tyr Leu Thr Gln Glu His Leu Val Glu Phe Cys
        195                 200                 205 aaa tta cac gat atc caa gta gtt gct tac tcc tcc ttc ggt cct caa         1152
Lys Leu His Asp Ile Gln Val Val Ala Tyr Ser Ser Phe Gly Pro Gln
    210                 215                 220 tca ttc att gag atg gac tta cag ttg gca aaa acc acg cca act ctg         1200
Ser Phe Ile Glu Met Asp Leu Gln Leu Ala Lys Thr Thr Pro Thr Leu
225                 230                 235                 240 ttc gag aat gat gta atc aag aag gtc tca caa aac cat cca ggc agt         1248
Phe Glu Asn Asp Val Ile Lys Lys Val Ser Gln Asn His Pro Gly Ser
                245                 250                 255 acc act tcc caa gta ttg ctt aga tgg gca act cag aga ggc att gcc         1296
Thr Thr Ser Gln Val Leu Leu Arg Trp Ala Thr Gln Arg Gly Ile Ala
            260                 265                 270 gtc att cca aaa tct tcc aag aag gaa agg tta ctt ggc aac cta gaa         1344
Val Ile Pro Lys Ser Ser Lys Lys Glu Arg Leu Leu Gly Asn Leu Glu
        275                 280                 285 atc gaa aaa aag ttc act tta acg gag caa gaa ttg aag gat att tct         1392
Ile Glu Lys Lys Phe Thr Leu Thr Glu Gln Glu Leu Lys Asp Ile Ser
    290                 295                 300 gca cta aat gcc aac atc aga ttt aat gat cca tgg acc tgg ttg gat         1440
Ala Leu Asn Ala Asn Ile Arg Phe Asn Asp Pro Trp Thr Trp Leu Asp
305                 310                 315                 320 ggt aaa ttc ccc act ttt gcc tgatccagcc agtaaaatcc atactcaacg            1491
Gly Lys Phe Pro Thr Phe Ala
                325 acgatatgaa caaatttccc tcattccgat gctgtatatg tgtataaatt tttacatgct       1551 cttctgttta gacacagaac agcttttaaat aaaatgttgg atatactttt tctgcctgtg      1611 gtgtcatcca cgcttttaat tcatctcttg tatggttgac aatttggcta ttttttaaca      1671 gaacccaacg gtaattgaaa ttaaaaggga aacgagtggg ggcgatgagt gagtgatact       1731 aaaatagaca ccaagagagc aaagcggtcc caaaatcatt tgagtaaccg gatatctatc      1791 gggatattaa tagcagcttc catttcaact aaaacaacag caagat atg agc gac          1846
                                                Met Ser Asp
                                                    1 aag atatccttc tacctcccga acccatccaa ctacttgacg aagactccac               1899
Lys ggagcctgaa ctcgacattg a                                                 1920

<210> SEQ ID NO 2
<211> LENGTH: 42
<212> TYPE: DNA
<213> ORGANISM: Saccharomyces cerevisiae

<400> SEQUENCE: 2
gcgctgatca tctagaatgt acgagcccaa accggagcac ag                          42

<210> SEQ ID NO 3
<211> LENGTH: 42
<212> TYPE: DNA
<213> ORGANISM: Saccharomyces cerevisiae

<400> SEQUENCE: 3
gctttgatca tctagatcac cccgcacccc caggaggta ct                           42
```

```
<210> SEQ ID NO 4
<211> LENGTH: 40
<212> TYPE: DNA
<213> ORGANISM: P. stipitis

<400> SEQUENCE: 4
gcggatcctc tagaatgcgt tctattaagt tgaactctgg                40

<210> SEQ ID NO 5
<211> LENGTH: 40
<212> TYPE: DNA
<213> ORGANISM: P. stipitis

<400> SEQUENCE: 5
ttggatcctc tagattagac gaagatagga atcttgtccc                40

<210> SEQ ID NO 6
<211> LENGTH: 27
<212> TYPE: DNA
<213> ORGANISM: P. stipitis

<400> SEQUENCE: 6
cgcaggatcc actagaatgc cttctat                              27

<210> SEQ ID NO 7
<211> LENGTH: 27
<212> TYPE: DNA
<213> ORGANISM: P. stipitis

<400> SEQUENCE: 7
tcctctagat tggacgaaga taggaat                              27

<210> SEQ ID NO 8
<211> LENGTH: 27
<212> TYPE: DNA
<213> ORGANISM: P. stipitis

<400> SEQUENCE: 8
gcgtctagaa tgactgctaa cccttcc                              27

<210> SEQ ID NO 9
<211> LENGTH: 34
<212> TYPE: DNA
<213> ORGANISM: P. stipitis

<400> SEQUENCE: 9
gcgcgaagct tagatcttta ctcagggccg tcaa                      34

<210> SEQ ID NO 10
<211> LENGTH: 23
<212> TYPE: DNA
<213> ORGANISM: P. stipitis

<400> SEQUENCE: 10
gcctctagaa tgcctttatt aag                                  23

<210> SEQ ID NO 11
<211> LENGTH: 34
<212> TYPE: DNA
<213> ORGANISM: P. stipitis

<400> SEQUENCE: 11
gcgcgaagct tggatcctta gacgaagata ggaa                      34
```

<210> SEQ ID NO 12
<211> LENGTH: 33
<212> TYPE: DNA
<213> ORGANISM: P. stipitis

<400> SEQUENCE: 12
cgcaggatcc actagaatga ctgctaaccc ttc                          33

<210> SEQ ID NO 13
<211> LENGTH: 28
<212> TYPE: DNA
<213> ORGANISM: P. stipitis

<400> SEQUENCE: 13
tcctctagaa ccctcagggc cgtcaatg                               28

<210> SEQ ID NO 14
<211> LENGTH: 54
<212> TYPE: DNA
<213> ORGANISM: P. stipitis

<400> SEQUENCE: 14
gcctctagac catctccaac cgctagcact aaccaaatgc cttctattaa gttg   54

<210> SEQ ID NO 15
<211> LENGTH: 37
<212> TYPE: DNA
<213> ORGANISM: E. coli

<400> SEQUENCE: 15
gcgcgagatc ttctagaatg cgaattggca taccaag                     37

<210> SEQ ID NO 16
<211> LENGTH: 39
<212> TYPE: DNA
<213> ORGANISM: E. coli

<400> SEQUENCE: 16
cgcgcagatc ttctagatta atttttgcgg aacattttc                   39

<210> SEQ ID NO 17
<211> LENGTH: 34
<212> TYPE: DNA
<213> ORGANISM: E. coli

<400> SEQUENCE: 17
gcgcgagatc taaaatgtct ggaggattag ttac                        34

<210> SEQ ID NO 18
<211> LENGTH: 32
<212> TYPE: DNA
<213> ORGANISM: E. coli

<400> SEQUENCE: 18
cgcgcagatc tttacagagc tttcaggatt gc                          32

<210> SEQ ID NO 19
<211> LENGTH: 27
<212> TYPE: DNA
<213> ORGANISM: A. vinelandii
<220> FEATURE:
<223> OTHER INFORMATION: "n" bases represent A, T, C, G, other or
      unknown

```
<400> SEQUENCE: 19
gtntayaayt aygaygtngt ngtnath                              27

<210> SEQ ID NO 20
<211> LENGTH: 27
<212> TYPE: DNA
<213> ORGANISM: A. vinelandii
<220> FEATURE:
<223> OTHER INFORMATION: "n" bases represent A, T, C, G, other or
      unknown

<400> SEQUENCE: 20
rtarttraan gtngtrttda traarta                              27

<210> SEQ ID NO 21
<211> LENGTH: 30
<212> TYPE: DNA
<213> ORGANISM: P. stipitis

<400> SEQUENCE: 21
ggatccagat ctatggacta ctcatacgct                           30

<210> SEQ ID NO 22
<211> LENGTH: 30
<212> TYPE: DNA
<213> ORGANISM: P. stipitis

<400> SEQUENCE: 22
ggatccagat ctttaaactg tgggtcgtat                           30

<210> SEQ ID NO 23
<211> LENGTH: 35
<212> TYPE: DNA
<213> ORGANISM: Saccharomyces cerevisiae

<400> SEQUENCE: 23
gcggatcctc tagaatggtt tgttcagtaa ttcag                     35

<210> SEQ ID NO 24
<211> LENGTH: 33
<212> TYPE: DNA
<213> ORGANISM: Saccharomyces cerevisiae

<400> SEQUENCE: 24
agatctggat ccttagatga gagtcttttc cag                       33

<210> SEQ ID NO 25
<211> LENGTH: 35
<212> TYPE: DNA
<213> ORGANISM: Saccharomyces cerevisiae

<400> SEQUENCE: 25
gatcgaattc tttgtaactg taatttcact catgc                     35

<210> SEQ ID NO 26
<211> LENGTH: 33
<212> TYPE: DNA
<213> ORGANISM: Saccharomyces cerevisiae

<400> SEQUENCE: 26
gtacaagctt tttccaattt tcctttacga ttt                       33

<210> SEQ ID NO 27
```

-continued

```
<211> LENGTH: 33
<212> TYPE: DNA
<213> ORGANISM: Saccharomyces cerevisiae

<400> SEQUENCE: 27
gatcaagctt aatccatact caacgacgat atg                                    33

<210> SEQ ID NO 28
<211> LENGTH: 31
<212> TYPE: DNA
<213> ORGANISM: Saccharomyces cerevisiae

<400> SEQUENCE: 28
gtacggatcc gtcgctcata tcttgctgtt g                                      31

<210> SEQ ID NO 29
<211> LENGTH: 327
<212> TYPE: PRT
<213> ORGANISM: Saccharomyces cerevisiae

<400> SEQUENCE: 29
```

Met Ser Ser Leu Val Thr Leu Asn Asn Gly Leu Lys Met Pro Leu Val
 1               5                  10                  15

Gly Leu Gly Cys Trp Lys Ile Asp Lys Lys Val Cys Ala Asn Gln Ile
            20                  25                  30

Tyr Glu Ala Ile Lys Leu Gly Tyr Arg Leu Phe Asp Gly Ala Cys Asp
        35                  40                  45

Tyr Gly Asn Glu Lys Glu Val Gly Glu Gly Ile Arg Lys Ala Ile Ser
    50                  55                  60

Glu Gly Leu Val Ser Arg Lys Asp Ile Phe Val Val Ser Lys Leu Trp
65                  70                  75                  80

Asn Asn Phe His His Pro Asp His Val Lys Leu Ala Leu Lys Lys Thr
                85                  90                  95

Leu Ser Asp Met Gly Leu Asp Tyr Leu Asp Leu Tyr Tyr Ile His Phe
            100                 105                 110

Pro Ile Ala Phe Lys Tyr Val Pro Phe Glu Glu Lys Tyr Pro Pro Gly
        115                 120                 125

Phe Tyr Thr Gly Ala Asp Asp Glu Lys Lys Gly His Ile Thr Glu Ala
    130                 135                 140

His Val Pro Ile Ile Asp Thr Tyr Arg Ala Leu Glu Glu Cys Val Asp
145                 150                 155                 160

Glu Gly Leu Ile Lys Ser Ile Gly Val Ser Asn Phe Gln Gly Ser Leu
                165                 170                 175

Ile Gln Asp Leu Leu Arg Gly Cys Arg Ile Lys Pro Val Ala Leu Gln
            180                 185                 190

Ile Glu His His Pro Tyr Leu Thr Gln Glu His Leu Val Glu Phe Cys
        195                 200                 205

Lys Leu His Asp Ile Gln Val Val Ala Tyr Ser Ser Phe Gly Pro Gln
    210                 215                 220

Ser Phe Ile Glu Met Asp Leu Gln Leu Ala Lys Thr Thr Pro Thr Leu
225                 230                 235                 240

Phe Glu Asn Asp Val Ile Lys Lys Val Ser Gln Asn His Pro Gly Ser
                245                 250                 255

Thr Thr Ser Gln Val Leu Leu Arg Trp Ala Thr Gln Arg Gly Ile Ala
            260                 265                 270

Val Ile Pro Lys Ser Ser Lys Lys Glu Arg Leu Leu Gly Asn Leu Glu
        275                 280                 285

```
Ile Glu Lys Lys Phe Thr Leu Thr Glu Gln Glu Leu Lys Asp Ile Ser
    290                 295                 300

Ala Leu Asn Ala Asn Ile Arg Phe Asn Asp Pro Trp Thr Trp Leu Asp
305                 310                 315                 320

Gly Lys Phe Pro Thr Phe Ala
                325

<210> SEQ ID NO 30
<211> LENGTH: 4
<212> TYPE: PRT
<213> ORGANISM: Saccharomyces cerevisiae

<400> SEQUENCE: 30

Met Ser Asp Lys
1
```